United States Patent [19]

Zlotnik

[11] 4,452,500
[45] Jun. 5, 1984

[54] TAMPER-RESISTANT DEODORANT CABINET

[76] Inventor: Arnold H. Zlotnik, 1000 Sullivan Dr., Homestead, Pa. 15120

[21] Appl. No.: 366,294

[22] Filed: Apr. 7, 1982

[51] Int. Cl.³ .................. A47B 77/08; A62B 7/08
[52] U.S. Cl. ..................... 312/236; 312/245; 220/339; 292/254; 422/123
[58] Field of Search ............. 312/236, 211, 212, 245, 312/31.1, 31.3, 311; 422/123, 124, 5; 220/81, 339; 206/1.5; 239/44; 292/254

[56] References Cited

U.S. PATENT DOCUMENTS

| | | | |
|---|---|---|---|
| 113,862 | 4/1871 | Duffett | 312/245 |
| 1,133,254 | 3/1915 | Backus | 292/254 |
| 1,254,337 | 1/1918 | Marsh | 422/124 |
| 1,379,228 | 5/1921 | Swift | 312/245 |
| 1,588,351 | 6/1926 | Grossnickle | 292/254 |
| 2,115,720 | 5/1938 | Holmes | 312/236 |
| 2,234,021 | 3/1941 | Castrique | 422/123 |
| 2,576,303 | 11/1951 | Matter | 312/245 |
| 2,828,953 | 4/1958 | Hartmann | 239/44 |
| 3,125,407 | 3/1964 | Kagan | 206/1.5 |
| 3,768,104 | 10/1973 | Sanderson | 422/5 |
| 3,885,738 | 5/1975 | Chesmel et al. | 239/44 |
| 4,189,195 | 2/1980 | Turney | 312/245 |
| 4,202,464 | 5/1980 | Mohs et al. | 220/339 |
| 4,244,495 | 1/1981 | Lorscheid et al. | 220/339 |
| 4,339,079 | 7/1982 | Sato et al. | 422/123 |

Primary Examiner—Victor N. Sakran
Attorney, Agent, or Firm—Reed, Smith, Shaw & McClay

[57] ABSTRACT

A deodorant cabinet wherein a cover (14) is hinged to a back plate (10). The cabinet is maintained in the closed position by a latch (36) that cooperates with a protruding member (32) connected to a strike plate (28). The cabinet is opened by insertion of a key (40) through a keyway (42) in cover (14) to deflect strike plate (28) and disengage engaging member (32) from latch (36). The cabinet further includes a fan (48) that draws air past deodorant material on shelf (12) and expels it through louvers (38).

5 Claims, 7 Drawing Figures

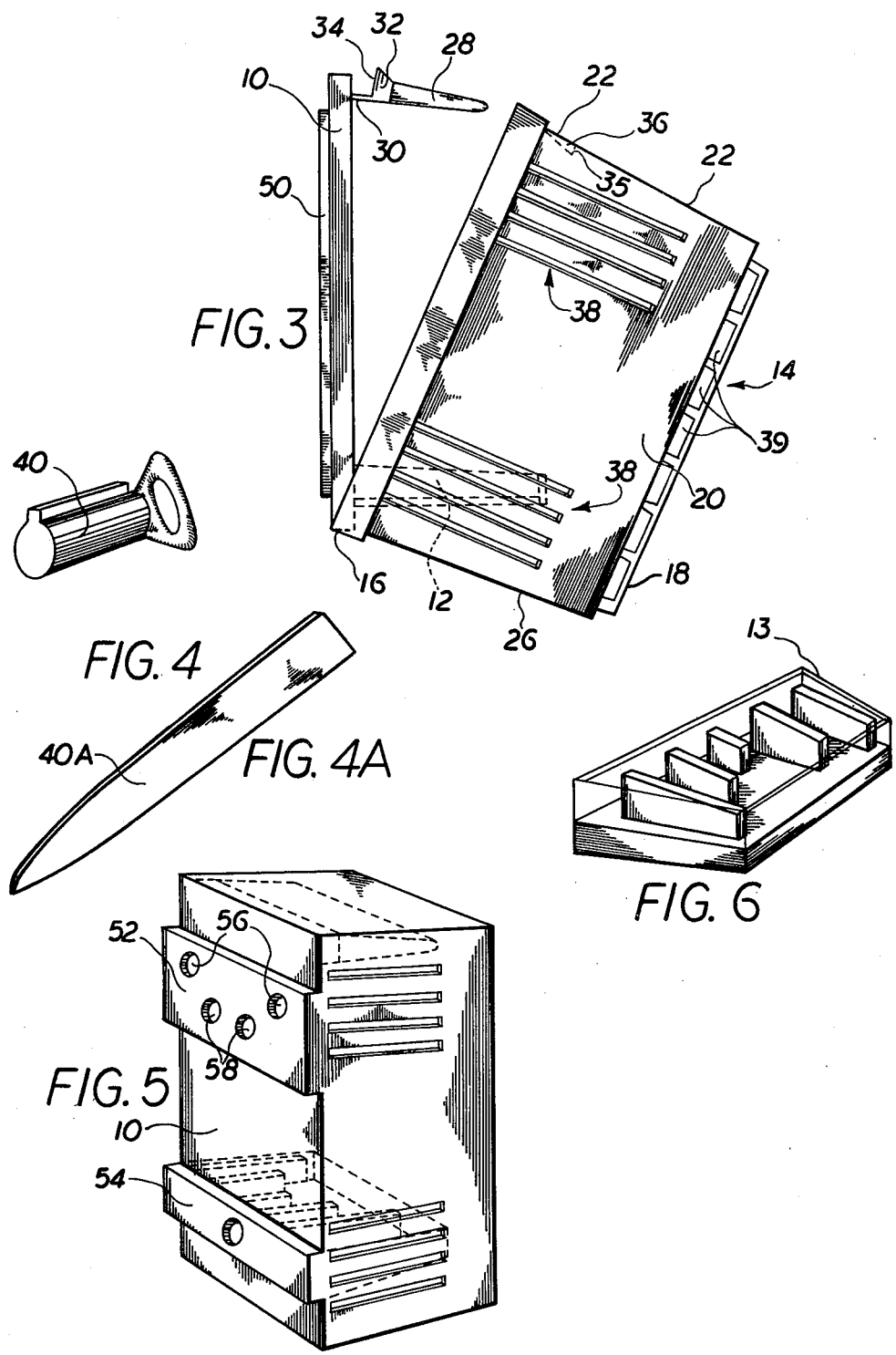

TAMPER-RESISTANT DEODORANT CABINET

BACKGROUND OF THE INVENTION

1. Field of the Invention

The subject invention is related to cabinets for dispensing deodorants and, more particularly, to tamper-resistant cabinets for dispensing deodorants.

2. Description of the Prior Art

In the prior art, various types of cabinets have been developed for containing deodorants and odor counteractants. Examples are shown in U.S. Pat. Nos. 3,125,407 and 3,885,738.

One disadvantage with many cabinets known in the prior art has been that they can be readily opened so that the deodorant material is subject to unauthorized removal. While some cabinets have been said to be tamper-proof, they have been generally more complex and, therefore, more expensive to make and troublesome to use. Accordingly, there was a need in the prior art for an inexpensive cabinet that was tamper-resistant so as to protect the deodorant material from loss but that was simple to use and maintain.

SUMMARY OF THE INVENTION

In accordance with the subject invention, a tamper-resistant deodorant dispenser cabinet includes a back plate having a shelf that supports the deodorizing material. A cover member which is hinged to the back plate includes a latch means on an internal surface thereof. The end of the cover having the internal latch is also provided with at least one keyway. A strike plate that includes an engaging member is connected to the back plate in a flexible, resilient member. The engaging member, which preferably has a generally sawtooth shape, is positioned such that it engages the internal latch of the cover to maintain the cover closed when the strike plate is in the normal position, but allows passage of the internal latch and permits the cover to be pivoted away from the back plate when the strike plate is biased in a first direction into a flexed position. The subject invention also includes a key that is insertable through the keyway to engage and bias the strike plate to move the engaging member out of engagement with the internal latch and permit the cover to be pivoted away from the back plate.

Preferably, ribs or mounting brackets are provided on the back of the back plate to space the back plate away from the mounting surface. Also preferably, the cabinet is provided with a fan that projects air toward the front wall of the cover, thereby drawing air into the cabinet through louvers in the sidewalls thereof to flow around the deodorizing material. More preferably, the shelf that supports the deodorizing material includes a tray having dividers that are spaced apart such that they maintain the deodorizing material on one edge so that exposure of the deodorizing material to the air flow is increased.

Other details, objects and advantages of the invention will become apparent as the following description of a presently preferred embodiment thereof proceeds.

BRIEF DESCRIPTION OF THE DRAWINGS

The accompanying drawings show a presently preferred embodiment of the subject invention in which:

FIG. 3 is a side elevation of the cabinet shown in FIG. 1 except that the cover is in the open position;

FIG. 4 shows a key useful in the practice of the subject invention;

FIG. 4A shows a second key useful in the practice of the subject invention;

FIG. 5 is a perspective view of an alternative embodiment of a deodorant cabinet in accordance with the subject invention; and FIG. 6 is a perspective view of a tray for supporting deodorant materials in accordance with the subject invention.

DESCRIPTION OF THE PREFERRED EMBODIMENT

Figure 1:
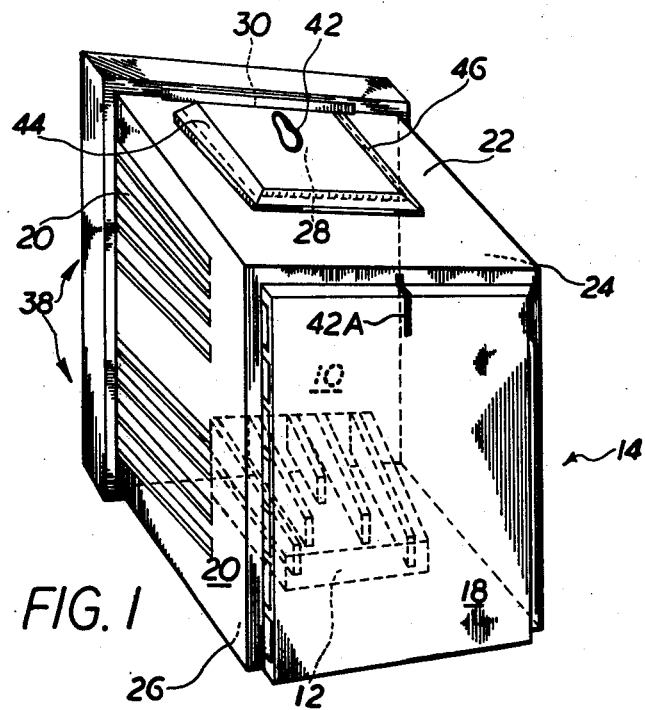
FIG. 1 is a perspective view of a deodorant cabinet in accordance with the subject invention.
Figure 2:
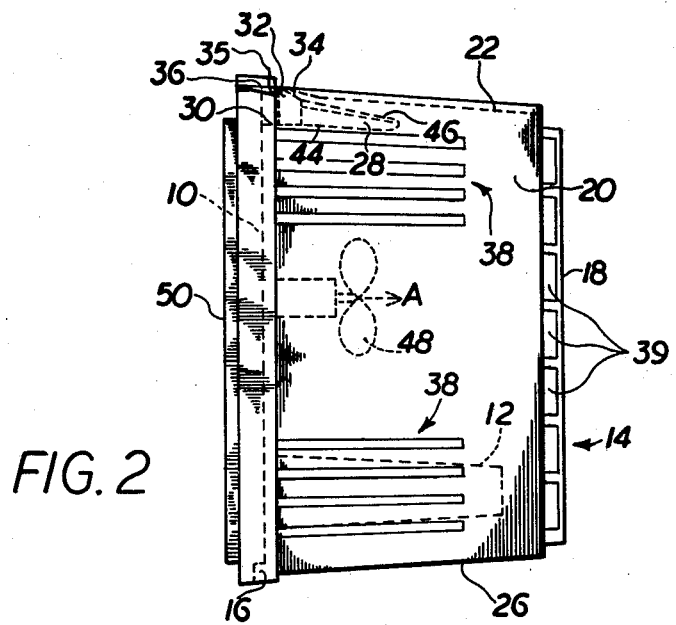
FIG. 2 is a side elevation of the cabinet shown in FIG. 1.

As shown in FIGS. 1-3, the deodorant cabinet of the subject invention includes a back plate 10 that is suitably arranged with slots and screw holes for convenient mounting on a vertical surface. A shelf 12 is connected to back plate 10 to support deodorant material placed in the cabinet. Preferably, and with reference also to FIG. 6, a tray 13 is provided to rest within shelf 12 and includes a plurality of dividers that are spaced apart such that the deodorant material is received therebetween and maintained on its edge. In this way, the deodorant material is better exposed to air flow through the cabinet, as discussed more fully below.

A cover 14 is connected to back plate 10, e.g., adjacent the bottom edge thereof, by a hinge 16, such that cover 14 can be pivoted between the closed position shown in FIGS. 1 and 2 and the open position shown in FIG. 3. Hinge 16 can be a conventional hinge or, where the dispenser cabinet is made of molded plastic or a similar material, hinge 16 can be a thin plastic section that joins cover 14 and back plate 10. In the preferred embodiment, cover 14 includes front face 18 and sidewalls 20 and 24, top face 22 and bottom face, 26, arranged in a generally rectangular or trapezoidal shape. However, as will be apparent to those skilled in the art, cover 14 could be adapted so that it could include more or fewer sides of varying shape.

Adjacent the end of back plate 10 that is opposite from hinge 16, i.e., its top, back plate 10 is further provided with a strike plate 28 that is connected to back plate 10 by a flexible, resilient member 30. Strike plate 28 includes a protruding member 32 that is generally sawtooth in shape having a surface 34 that is adapted to engage the surface 35 of a latch 36 provided on the inner surface of cover 14. In the preferred embodiment, latch 36 is provided on the inner surface of top face 22. Alternatively, however, strike plate 28 could be aligned on back plate 10 such that the major plane of strike plate 28 was substantially parallel to sidewalls 20 or 24 and latch 36 could be provided on the inner surface of sidewalls 20 or 24, respectively.

To permit the flow of air through the cabinet in a manner to dispense the deodorant material, sidewalls 20 and 24 are provided with a plurality of sets of generally horizontally oriented louvers 38 in both upper and lower regions thereof to permit the ingress of air into the cabinet. Additionally, sidewalls 20 and 24 are provided with a plurality of generally vertically oriented slots 39 immediately adjacent the front face 18 to permit the egress of deodorized air from the cabinet, in a manner to be discussed more fully hereinbelow.

To impede unauthorized opening of the disclosed cabinet, the subject invention includes a key 40 having a characteristic cross-section. As shown in FIG. 4, the cross-section of key 40 may be that of a circle with a rectangular section extending therefrom. Alternatively and as shown in FIG. 4A, key 40A may be conveniently shaped similar to a common nail file, i.e., thin with a pointed end and arcuate surfaces extending therefrom. Thus, generally key 40 can be provided with any cross-section that is sufficiently unique and convenient. The front face 18 or at least one of walls 20-26 of cover 14 is provided with a keyway 42 (shown only in FIG. 1) that has a shape corresponding to the cross-section of key 40. In one embodiment of the invention, keyway 42 is provided in the topface 22 of cover 14. Alternatively and preferably with use of the key 40A shown in FIG. 4A, a keyway 42A can be provided in front face 18 of cover 14 adjacent the top thereof facing the strike plate 28 when the cover 14 is in its closed position. Where a keyway 42 is provided in a wall of cover 14 that does not include latch 36, strike plate 28 is slightly modified to provide a surface that intersects a line normal to the side and passing through the keyway. In the example of FIGS. 1-3, strike plate 28 may further include beveled sections 44 and 46.

As shown in FIGS. 1 and 2, protruding member 32 cooperates with latch 36 to maintain the cabinet in the closed position with cover 14 seated against backplate 10. To open the cabinet, key 40 is longitudinally inserted through keyway 42 until the end of key 40 engages strike plate 28 and deflects strike plate 28 in a direction away from topface 22. When strike plate 28 is sufficiently deflected, surface 34 of protruding member 32 disengaged surface 35 of latch 36 allowing cover 14 to pivot at hinge 16. In the embodiment of the invention including key 40A shown in FIG. 4A, the pointed end is inserted longitudinally through the keyway 42A in front face 18 until it adopts a position between the upper surface of strike plate 28 and the lower surface of the top face 22. Additional insertion of the key 40A biases the opposed arcuate surfaces thereof against the strike plate 28 and top face 22 to separate same and disengage latch 36 from protruding member 32. In this manner, as shown in FIG. 3, the cabinet may be placed in the "open" position by pivoting cover 14 downwardly.

Due to the resiliency of member 30, strike plate 28 returns to its initial position when cover 14 is pivoted downwardly and key 40 disengages strike plate 28. Therefore, to return the cabinet to its closed, locked position, key 40 is removed from keyway 42 and cover 14 is returned to its full, upright position as shown in FIGS. 1 and 2. In closing the cabinet, member 30 flexes in response to the engagement of protruding member 32 with latch 36 to allow protruding member 32 to pass over latch 36 and engage surface 35.

Although member 30 is flexible, it is selected to have sufficiently high flexure resistance that ordinary wire or similar commonly available materials that are of sufficiently small diameter to be inserted through keyway 42 will not provide the threshold tensile strength necessary to sufficiently deflect strike plate 28 to disengage protruding member 32 from latch 36. Therefore, the cabinet herein disclosed is relatively tamper-resistant requiring a key that uniquely corresponds to keyway 42. Yet the disclosed cabinet has a straightforward design that is economical and reliable.

Also in accordance with the subject invention, the disclosed cabinet may be provided with a motorized fan 48 (shown only in FIG. 2) that is attached to back plate 10 in a manner such that the fan blades generate a particularly advantageous air flow pattern in cooperation with louvers 38 and slots 39. In particular, fan 48 faces front face 18 and directs air flow immediately theretoward. This orientation has the general effect of drawing air away from the deodorizing material, rather than the conventional arrangement whereby air is propelled from a fan toward the deodorizing material. Fan 48 generates a vacuum condition which results in an ingress of air flow through louvers 38, which air flow passes the deodorizing material to controllably evaporate portions thereof, after which the deodorized air is propelled outwardly through slots 39.

In the prior art, motorized fans were used to direct air in the opposite direction on or across the deodorant material. However, in accordance with the subject invention, it has been found that fan 48 more effectively dispenses the deodorant by actually directing the air flow away from the deodorant material as indicated by the arrow A in FIG. 2.

Preferably, back plate 10 is also provided with ribs 50 that are attached on the side opposite from fan 48. Ribs 50 separate back plate 10 from the mounting surface and thus provide a channel for a wire to bring electrical service to fan 48.

FIG. 5 shows an alternative embodiment wherein back plate 10 is provided with lateral mounting brackets 52 and 54 for attaching the cabinet to the mounting surface. Preferably, bracket 52 is provided with first and second sets of holes 56 and 58 respectively. Holes 56 and 58 are arranged so that a plurality of types of motor and fan assemblies can be mounted from bracket 52. The disclosed cabinet can be secured to the mounting surface by fastening means such as screws or bolts or, alternatively, by two-sided tape.

While a preferred embodiment of the subject invention has been shown and described, it is to be understood that the invention is not limited thereto but may be otherwise variously embodied within the scope of the following claims.

What is claimed is:

1. A tamper-resistant cabinet for containing deodorant materials for dispersal into the atmosphere, comprising:

a back plate adapted for mounting to a supporting surface;

shelf means connected to said back plate and arranged to fit within said cover, said shelf means adapted to support a tray including dividers that are spaced apart such that said deodorant materials are received and maintained on one edge between said dividers;

a cover member having a keyway provided through at least one wall member thereof;

hinge means for pivotally fastening said cover member to said back plate to facilitate relative motion from an open position to a closed position therebetween, wherein said closed position defines a condition in which said deodorant materials are not removable from said cabinet, wherein said open position defines a condition in which said deodorant materials are removable from said cabinet;

latch means mounted on an internal surface of said cover member spaced from said hinge means;

a strike plate connected to said back plate having an engaging member of a general sawtooth from adapted for engaging said latch means when said cover member is disposed in said closed position to retain said cover member in said closed position; and flexible resilient connecting means for mounting said strike plate to said back plate within the interior of said cabinet when said cover member is in said closed position, wherein said strike plate is positioned to be biasable in a first direction whereby said connecting means is flexed to disengage said engaging member from said latch means only through the insertion of a suitably shaped rigid object through said keyway.

2. The cabinet of claim 1 further comprising:

ribs that are attached to said back plate facing said supporting surface, said ribs spacing the back plate away from said supporting surface to provide a channel between said surface and said back plate.

3. The cabinet of claim 1 wherein said cover member further comprises apertures in wall members thereof for the flow of air through said cabinet, said apertures spaced from said keyway such that said strike plate is not readily biasable in said first direction therethrough.

4. The cabinet of claim 1 further comprising:

fan means mounted within said cabinet to draw air away from said deodorant materials therein.

5. The cabinet of claim 1 further comprising:

mounting brackets that are attached to said back plate facing said supporting surface, said mounting brackets spacing the back plate away from said supporting surface and providing a means for mounting said cabinet to said supporting surface.

* * * * *